(12) United States Patent
Hatamura et al.

(10) Patent No.: US 6,554,799 B1
(45) Date of Patent: Apr. 29, 2003

(54) BIOLOGICAL PRECISION SCREW PUMP

(75) Inventors: Yotaro Hatamura, Tokyo (JP);
Masayuki Nakao, Chiba (JP);
Takenori Okusa, Tokyo (JP)

(73) Assignee: Center for Advanced Science and Technology Incubation, Ltd. (JP)

( * ) Notice: Subject to any disclaimer, the term of this patent is extended or adjusted under 35 U.S.C. 154(b) by 0 days.

(21) Appl. No.: 09/524,301

(22) Filed: Mar. 14, 2000

(30) Foreign Application Priority Data

Sep. 2, 1999 (JP) .......................................... 11-248784

(51) Int. Cl.[7] ................................................ A61M 1/00
(52) U.S. Cl. ...................... 604/151; 604/540; 415/73; 29/889
(58) Field of Search ................................. 604/118, 119, 604/131, 151, 540; 29/889, 889.3; 415/72, 73; 416/176, 177, 230

(56) References Cited

U.S. PATENT DOCUMENTS

| | | | | | |
|---|---|---|---|---|---|
| 179,696 | A | * | 7/1876 | Gaddy | 416/176 X |
| 534,428 | A | * | 2/1895 | Dean | 416/176 X |
| 1,526,548 | A | * | 2/1925 | Ingison | 416/176 |
| 4,834,724 | A | * | 5/1989 | Geiss et al. | 604/540 |
| 4,919,647 | A | * | 4/1990 | Nash | 604/151 X |
| 4,969,865 | A | * | 11/1990 | Hwang et al. | 604/151 X |
| 5,040,944 | A | * | 8/1991 | Cook | 415/72 |
| 5,092,844 | A | * | 3/1992 | Schwartz et al. | 604/151 |
| 5,261,877 | A | * | 11/1993 | Fine et al. | 604/540 |
| 5,588,812 | A | * | 12/1996 | Taylor et al. | 604/151 X |
| 5,643,215 | A | * | 7/1997 | Fuhrman et al. | 604/151 |
| 6,248,091 | B1 | * | 6/2001 | Voelker | 604/151 X |

OTHER PUBLICATIONS

Okusa et al., "Micro Pump for Extrusion of Exudate in Middle Ear," *Medical Electronics and Biomedical Engineering* 37:329 (Partial translation attached), Apr. 1999.

* cited by examiner

*Primary Examiner*—John Rivell
(74) *Attorney, Agent, or Firm*—Nixon Peabody LLP

(57) ABSTRACT

The present invention provides a suction and injection pump capable of transferring a sufficient amount of viscous liquid even with a very thin suction and injection pipe, thereby enabling suction or injection of a viscous liquid while minimizing invasion into a human body.

A pump according to the present invention effectively sucks or injects a viscous liquid by housing a very thin rotor in a cylindrical needle and positively transferring the liquid based on the mechanical configuration of the rotor. The configuration of the present invention reduces the diameter of a pipe while minimizing invasion into a human body.

21 Claims, 15 Drawing Sheets

FIG. 1

RELATIONSHIP BETWEEN VISCOSITY LEVEL AND THE INNER AND OUTER DIAMETERS OF THE SUCTION TOOL JUDGED BY DOCTOR

| LEVEL | INNER DIAMETER | OUTER DIAMETER |
|---|---|---|
| 1 | φ0.32 | φ0.5 |
| 2 | φ0.42 | φ0.6 |
| 3 | φ0.70 | φ1.0 |
| 4 | φ1.2 | φ1.5 |

HIGH VISCOSITY →

BIOLOGICAL PRECISION SCREW PUMP

FIELD OF THE INVENTION

The present invention relates to a pump for sucking or injecting a liquid from or into a living tissue, and in particular, to a precision screw pump suitable for sucking or injecting a viscous tissue fluid while minimizing invasion into the human body.

BACKGROUND OF THE INVENTION

Conventional methods for sucking a biological tissue fluid from or injecting a liquid into a living body transfer a liquid by applying a negative pressure to a pipe to suck the liquid or applying a positive pressure to the pipe to extrude the liquid.

A recent growing demand for treatment methods with less invasion requires reduction in the diameter of a pipe inserted into a living body. On the other hand, the pipe frictional resistance increases in proportion to the viscosity of a liquid while decreasing in proportion to the pipe diameter, and a driving force for transfer further decreases in proportion to the square of the decrease in pipe diameter. Thus, it is difficult to use a pipe of a small diameter to transfer a viscous liquid inherently having a large pipe frictional resistance (FIG. 1).

Thus, small-diameter pipes can inevitably be used only for liquids of a low viscosity, and large-diameter pipes must still be used to suck or inject viscous tissue fluids.

If, however, a large-diameter pipe is used, for example, to treat tympanitis, a large amount of eardrum is disadvantageously incised upon insertion of the suction pipe. Besides, the large diameter of the suction pipe limits sites from which viscous pus can be sucked.

Likewise, when a large pressure is required in injecting a liquid, for example, the cerebrospinal fluid, a thick pipe must pierce through the body in order to obtain a high pressure sufficient to press the liquid surface.

According to the prior art, the pipe frictional resistance increases relatively with a decrease in pipe diameter, whereby it has been very difficult to reduce the diameter of the pipe to the extent that invasion into the living body can be minimized while maintaining an effective amount of liquid transferred. In particular, since it has been almost impossible to suck or inject a viscous liquid, which requires a high pressure for suction or injection, using a pipe of a very small diameter, suction or injection of a viscous liquid with less invasion is very significant.

SUMMARY OF THE INVENTION

An object of the present invention is to provide a suction and injection pump that can transfer a sufficient amount of viscous liquid despite the use of a very thin suction and injection pipe in order to provide means for enabling a viscous liquid to be sucked or injected while minimizing invasion into the human body.

Having made research to achieve this object, the inventors have found that introduction of a screw pump structure enables a liquid to be transferred only by means of the rotation of a rotor without depending on a pressure for sucking or pressing the liquid, that a viscous liquid can be moved by increasing the number of rotations of the rotor, and that the pipe diameter can be reduced by twisting up a plurality of very thin filaments to obtain a rotor of a very small diameter that can be rotatably housed in a thin pipe.

The present invention was made based on the findings that the transfer capability improves consistently with a decrease in friction between an inner wall of a needle and a transferred liquid or between the rotor and the liquid and that the screw pump prevents the amount of liquid transferred from being affected by a large gap between an outer periphery of the rotor and the inner wall of the needle, as long as the liquid has a certain degree of high viscosity.

The present invention provides a pump capable of minimizing invasion into human bodies by housing a very thin rotor in a cylindrical needle and positively transferring a liquid based on the mechanical configuration of the rotor so as to effectively suck or inject a viscous liquid while using this configuration to reduce the pipe diameter.

More specifically, the present invention provides a precision screw pump for injecting or ejecting a liquid into or from a biological tissue, as described below.

(1) A needle-shaped precision screw pump of a very small diameter for injecting or ejecting a liquid into or from a biological tissue.

(2) A precision screw pump in an instrument for injecting or ejecting a liquid into or from a biological tissue, comprising a cylindrical thin needle having an introduction port at one end and a discharge port at the other end, and a cylinder connected to one end of the needle and having a larger diameter than the needle, wherein said cylindrical needle is a screw pump comprising a rotor housed in said needle for rotation along an axial direction thereof and a driver housed in said cylinder and connected to one end of said rotor for rotating the rotor, wherein said rotor is a rotor obtained by twisting up a plurality of filaments and is rotated in synchronism with the rotation of said driver to transfer a liquid through said thin pipe from said introduction port to said discharge port.

(3) The precision screw pump according to (2) wherein said cylindrical needle comprises a smooth-surface substance having a predetermined strength.

(4) The precision screw pump according to (2) or (3) wherein the filaments constituting said rotor are covered with the smooth-surface substance.

(5) The precision screw pump according to any one of (2) to (4) wherein said rotor has a screw angle set between 15 and 35° relative to a rotational center axis.

In addition, the present invention provides a rotor for a screw pump as described below.

(6) A rotor for a screw pump manufactured by twisting up a plurality of filaments into a screw.

Further, the present invention includes the following method for producing a photocurable resin the above rotor for a screw pump.

(7) A method for producing the rotor for a screw pump rotor according to (6), the method comprising
providing a plurality of filaments,
coating an adhesive on the filaments,
twisting up the filaments, and
curing the adhesive to give a screw pump rotor.

(8) The method according to (7), wherein the adhesive is a photocurable resin.

In addition, a basic concept of the present invention is a biological liquid injection and ejection instrument as described below.

(9) A biological liquid injection and ejection instrument comprising a micro screw pump formed of a hollow needle.

(10) A biological liquid injection and ejection instrument wherein a micro screw pump is formed of a hollow needle so that the hollow needle has a small diameter.

(11) A method of making a diameter of a hollow needle small, the method comprising making a hollow needle in the form of a micro screw pump.

DEFINITION OF TERMINOLOGY

The "needle-shaped or needle" constituting the present screw pump can be shaped like a hollow cylinder and may have a flat or sharp tip, as shown in FIGS. 2A and 2B, respectively.

The "introduction or discharge port" of the needle is not necessarily limited to predetermined one end. In other words, for liquid suction, a tip portion of the needle which is contacted with the surface of a liquid to be sucked is the introduction port, whereas a cylinder side of the needle is the discharge port. On the contrary, for liquid injection, one end of the needle which is connected to the cylinder is the introduction port, while another end of the needle which is inserted into a living body is the discharge port.

The liquid to be transferred by the present screw pump can improve its own fluidity in the needle when the rotor is moved, and includes not only a solated liquid, which has low viscosity but also a gelled liquid, which has high viscosity.

The "screw pump" constituting the present invention is comprised of a casing and a rotor so as to transfer a liquid by rotating the rotor. The "rotor" is any rotor having a structure such as a "thread" or a "screw structure," which can rotate a shaft to transfer the liquid in a fixed direction.

The "plurality of filaments" constituting the rotor according to the present invention may be such a material as natural, synthetic, and metallic fibers, which can provide very thin fibers and which can be twisted up. Any material can be used as these filaments as long as it meets the above requirement.

In addition, the "rotor obtained by twisting up" the plurality of filaments can be obtained by twisting up a plurality of filaments, and the filaments may be twisted in the left lay (Z twist) direction similarly to the thread of a right-handed screw or in the right lay (S twist) direction.

If the filaments are formed from a plastic material, a required rotor can be obtained simply by twisting up the filaments. If, however, the twisted materials are untwisted upon the rotation of the rotor, then a strong screw rotor can be obtained by applying an adhesive to the filaments before twisting them up and then curing the adhesive while maintaining the twisted state.

The rotor thus obtained may be soft enough to be bent upon rotation as long as it is prevented from being broken upon rotation.

According to the present invention, the filaments are coated or impregnated with the adhesive before twisting, and then the coated filaments are twisted up and cured. The "adhesive" for use in the present invention may be any adhesive, for example, anaerobic, thermosetting, or optically curing, as long as it can prevent a screw shape obtained through twisting from returning to the original shape after curing. A photocurable resin is preferred since it can be coated thin on the surface of the filaments and can be simply cured.

The "photocurable resin," as used herein, refers to a resin containing an oligomer having one or more functional groups in the molecule which can react to light irradiation to form a crosslinking structure, a monomer having one or more similar functional groups in the molecule, or both of such a oligomer and monomer. The oligomer includes a radical-polymerized photocurable resin such as an unsaturated polyester-based resin, an acrylic-based resin, an en-thiol-based resin, or a cationic-polymerized photocurable resin such as an epoxy-based resin (of course, a mixture of a novolak resin with a sulfonate of a diazonaphthoquinone, which is a photosensitive agent, may be used). Of these resins, the acrylic-based resin, particularly, an ester acrylate, an urethane acrylate, or an epoxy acrylate is preferred as the oligomer contained in the photocurable resin according to the present invention. In addition, the above monomer includes monomers for radical polymerization such as acrylic esters and methacrylic esters and monomers for cationic polymerization such as epoxy-containing compounds. The monomer for radical polymerization is preferred due to its curing speed and physical properties exhibited after curing.

The "screw angle set between 15 and 35° relative to a rotational center axis" refers to an angle at which the screw is formed relative to the rotational center axis as shown in FIG. 3. This range of angles represents the screw angle at which the liquid transfer capability of the screw pump according to the present invention can be improved, and those values which slightly deviate from this range are also included within the technical scope of the present invention if they similarly improve liquid transfer capability.

The "smooth-surface substance having a predetermined strength" should be strong enough to avoid deformation even if the needle is inserted into the living body, and have smoothness enough to lessen the interfacial friction between an inner wall of the needle and a liquid flowing through the needle. Such a substance includes, for example, metal, metal with a predetermined coating, or plastic, and the plastic is preferred in terms of moldability.

The "smoothness" refers to being smooth, and a rough material surface such as a metallic machined surface or an electrically discharged surface is not preferred.

BRIEF DESCRIPTION OF THE DRAWINGS

FIG. 1 is a chart showing a conventional technique for use in the field to which the present invention belongs.

FIG. 8A represents suction and FIG. 8B represents injection.

DESCRIPTION OF NUMERALS

Figure 2A:
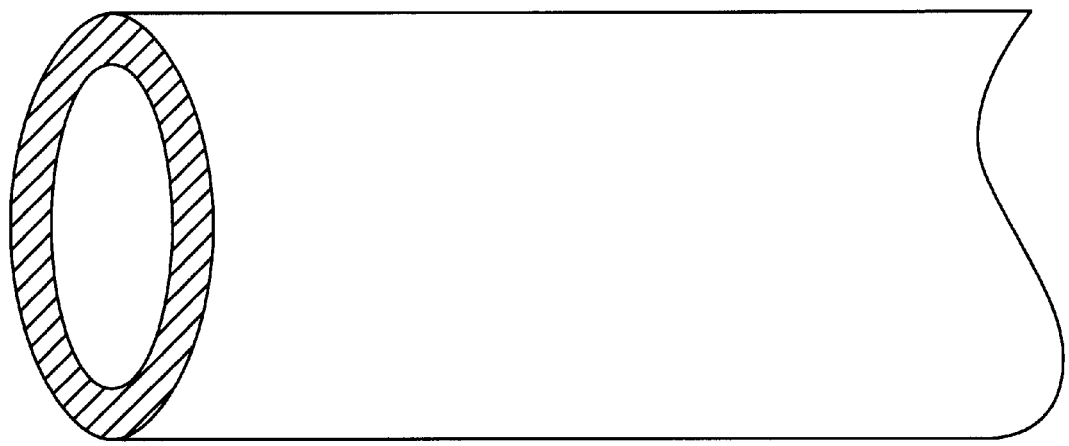
FIGS. 2A and 2B are block diagrams of the shapes of two needles according to the present invention.
Figure 2B:
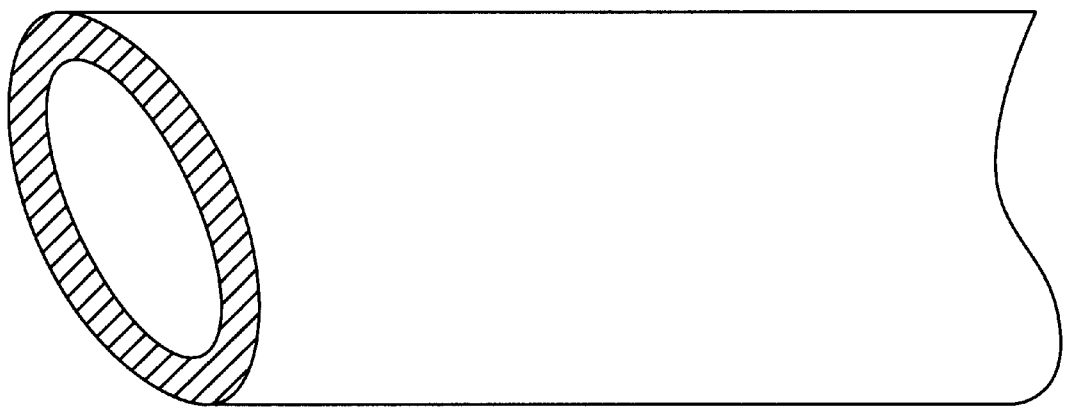
Figure 3:
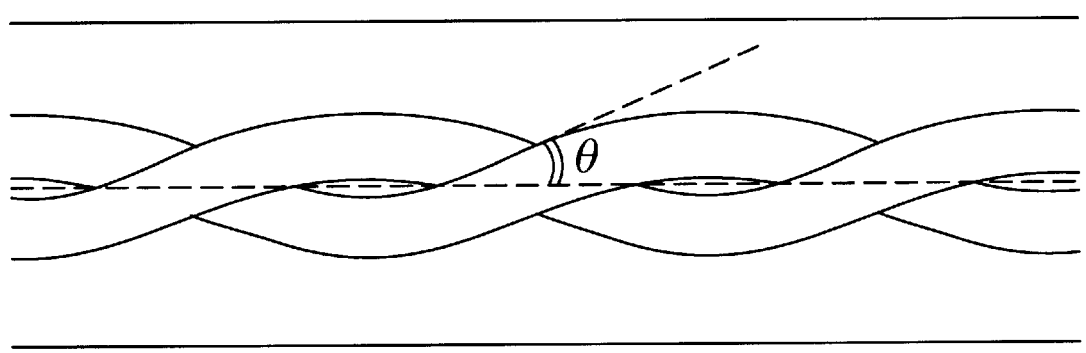
FIG. 3 is a block diagram of a screw angle relative to a rotational center axis of a rotor according to the present invention.

1 Cylindrical pipe
2 Tip portion of pipe
10 Cylinder
20 Rotor
30 Driver
31 Rotating shaft
40 Joining section
51 and 52 Filaments
53 Ultraviolet light
60 Gap between rotor outer peripheral portion and pipe inner wall

DETAILED DESCRIPTION OF THE INVENTION

A preferred embodiment of the present invention will be shown below.

Figure 4:
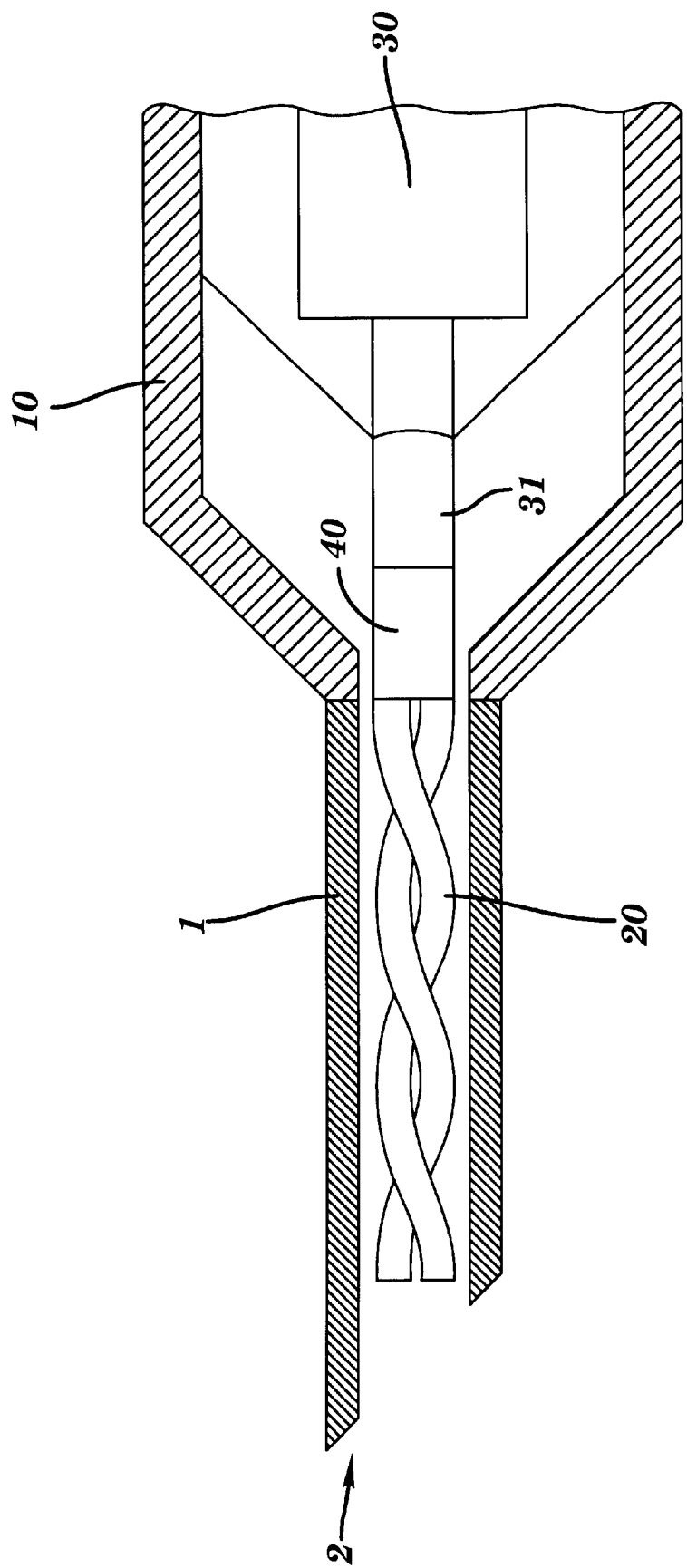
FIG. 4 is a sectional block diagram of a functional configuration of a precision screw pump according to the preferred embodiment of the present invention.

As shown in FIG. 4, a precision screw pump according to the embodiment of the present invention is comprised of a case section containing a cylindrical pipe 1 and a cylinder 10 connected to the pipe 1, and a rotation section rotatably housed in the case section containing a driver 30 having a rotating shaft 31 joined with the rotor 20 obtained by twisting up two filaments via a joining section 40.

Needle Shape

As shown in FIG. 4, the pipe 1 has a sharp tip portion 2 shaped for easy insertion into a living body.

Manufacture of Rotor

Figure 5A:
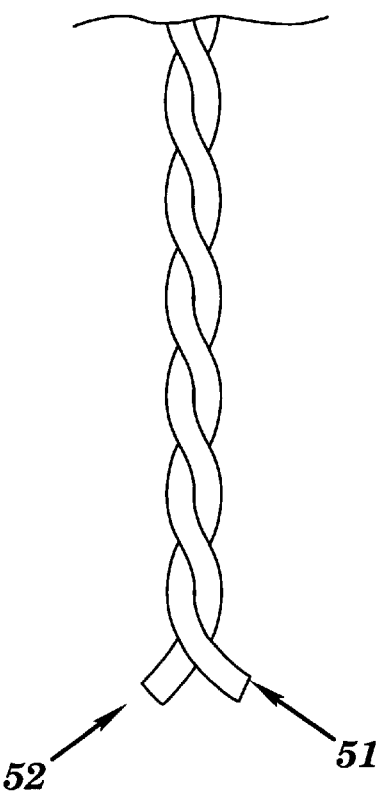
FIGS. 5A and 5B are block diagrams showing a process for manufacturing a rotor according to the preferred embodiment of the present invention.
Figure 5B:
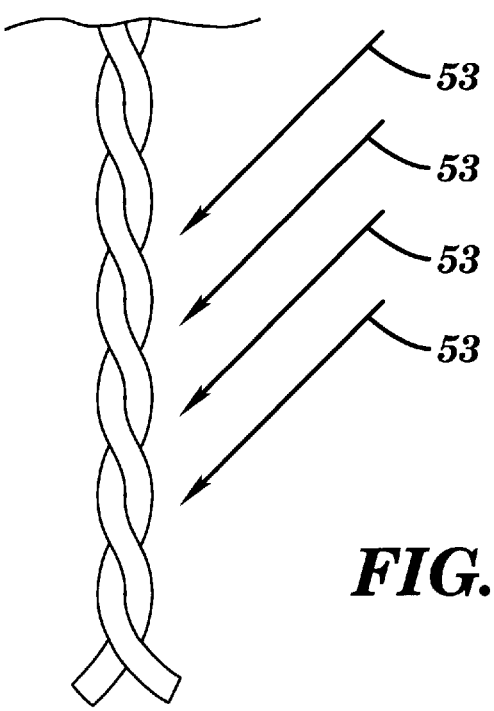

As shown in FIGS. 5A and 5B, the rotor according to the embodiment of the present invention can be obtained by coating a photocurable resin on the surface of a pair of very thin filaments 51 and 52, twisting up the filaments in the right lay (S twist) direction to form a screw (FIG. 5A), and irradiating the screw with an ultraviolet light 53 while maintaining the twisted state in order to cure and solidify the photocurable resin so as to avoid untwisting (FIG. 5B).

Transfer of Liquid

Figure 6:
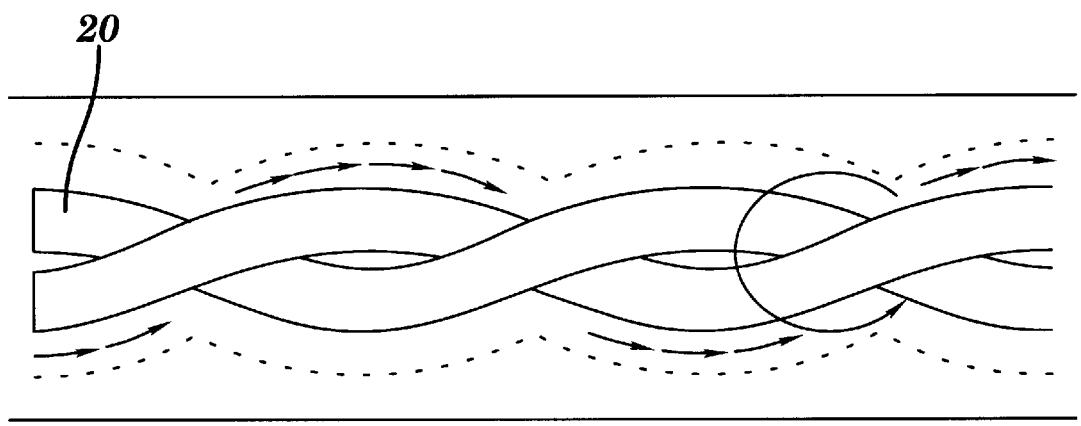
FIG. 6 is a block diagram showing transfer of a liquid through the screw pump according to the present invention.

As shown in FIG. 6, in the screw pump according to the present invention, a liquid flows along the screw shape of the rotor when the rotor 20 is rotated.

In addition, since the amount of liquid transferred by the screw pump can be increased by raising the rotation speed of the rotor 20 without any special external pressure, a viscous liquid can be transferred by augmenting the rotation speed even with a reduced diameter of the pipe.

Insertion into Living Body

Figure 7:
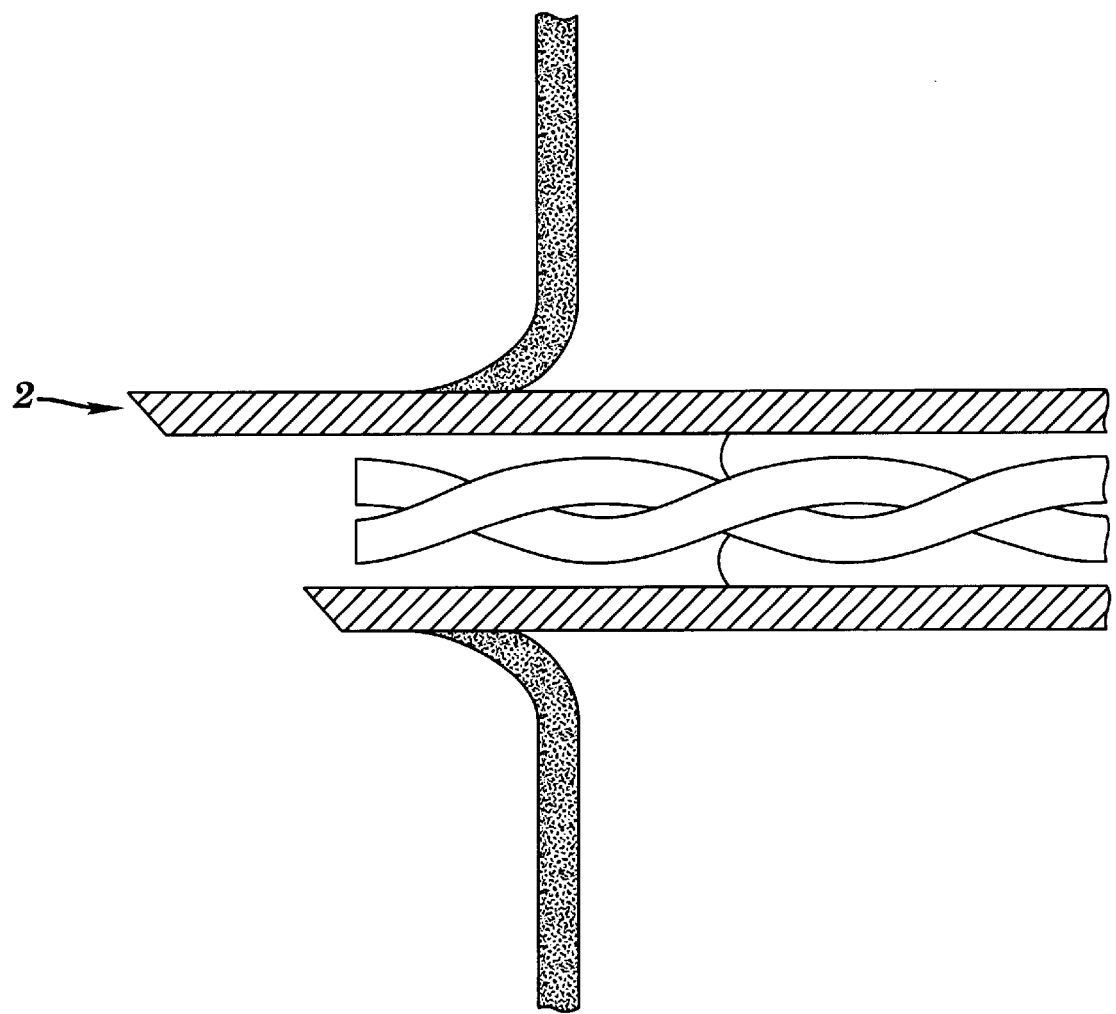
FIG. 7 is a block diagram showing insertion of the precision screw pump according to the preferred embodiments of the present invention into a living body.

As shown in FIG. 7, if the screw pump according to the embodiment of the present invention is inserted into a living body, invasion into the living body can be minimized because the screw pump has a small outer diameter and because the tip 2 of the needle is sharp.

Suction of Liquid

Figure 8A:
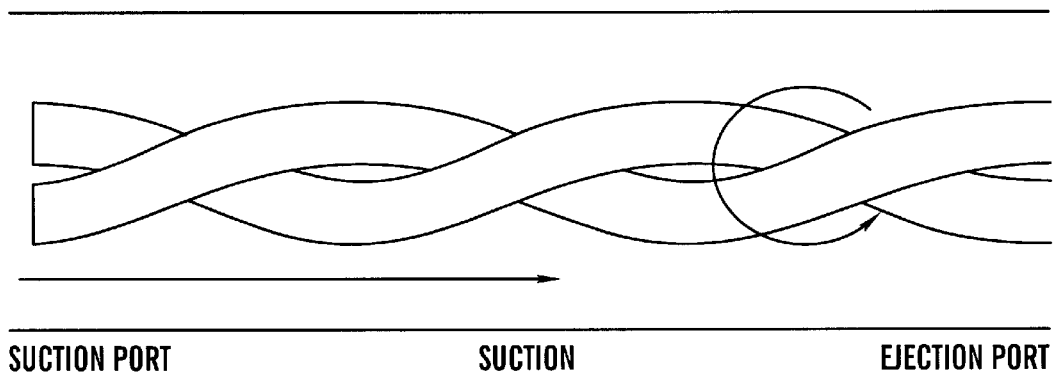
FIGS. 8A and 8B are block diagrams showing suction and injection of a liquid using the precision screw pump according to the preferred embodiment of the present invention.

When the screw pump is inserted into a living body at a target location and a biological tissue fluid is sucked, the rotor is rotated in the same direction as the twisting direction thereof (the direction in which the rotation untwists the screw) as shown in FIG. 8A.

This operation transfers the target liquid through pipe from a suction port to an ejection port, from which the liquid is finally ejected.

Injection of Liquid

Figure 8B:
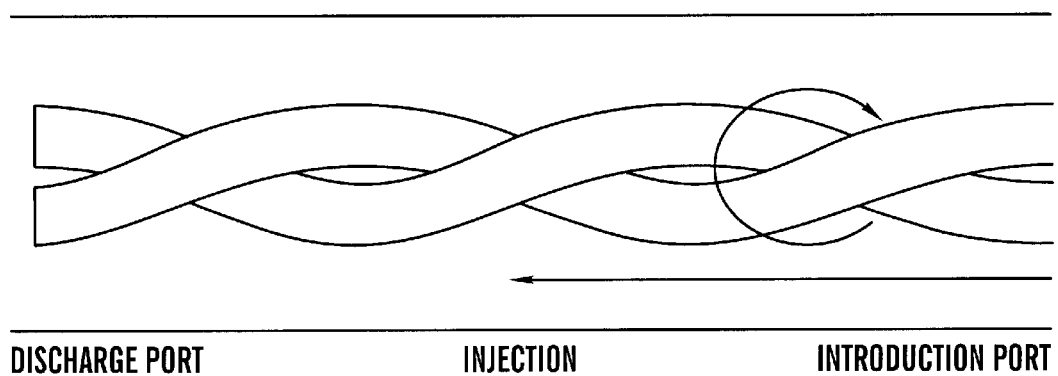

For liquid injection, the rotor is rotated in a direction opposite to the twisting direction of the rotor (the direction in which the rotation further tightens the screw) as shown in FIG. 8B.

This operation introduces a desired liquid through an introduction port and then transfers it through the pipe to a discharge port for injection.

This configuration enables the use of a pipe of a small diameter even if a viscous liquid is to be sucked or injected. Consequently, invasion into the living body can be minimized, while a viscous liquid can be sucked or injected.

Screw Angle

To set the screw angle relative to a rotational center axis between 15 and 35°, the number of times that the filaments are twisted and the screw pitch can be adjusted. In addition, the angle can be fixed at a certain angle by producing a rotor set at a desired angle relative to the center axis and coating the photocurable resin on the rotor for curing.

Gap between Rotor Outer Peripheral Portion and Pipe Inner Wall

Figure 9:
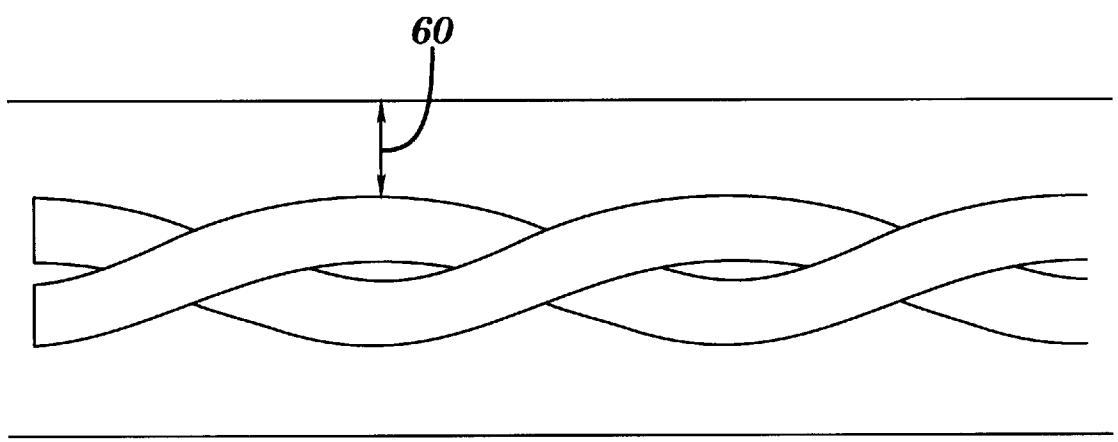
FIG. 9 is a block diagram of a gap between the rotor and an inner wall of a pipe in the screw pump according to the preferred embodiment of the present invention.

As shown in FIG. 9, a predetermined gap is set between the rotor and an inner wall of the pipe in the screw pump according to the embodiment of the present invention. The inventors have found that such a gap does not affect the operation for transferring a viscous liquid using the screw pump if the number of rotations of a screw portion is sufficiently high (about 15,000 rpm or more), and that such a gap is sufficient to allow the screw pump to provide an appropriate performance.

The "predetermined gap" can be set appropriately by those skilled in the art taking into consideration the thickness of a layer of a liquid transferred inside the needle along the outer periphery of the rotor and difficulties in assembling the screw pump.

For example, the gap should be narrowed for a liquid of a low viscosity, whereas it should be widened for a liquid of a high viscosity. The size of this gap is preferably 50 $\mu$m or more in terms of the assembly easiness with which the rotor is housed in the needle.

The present invention provides a very thin rotor that enables reducing the diameter of a pipe to be inserted into a living body. In addition, since the present invention enables transferring a viscous liquid even with a pipe of a small diameter, the performance of sucking or injecting a viscous liquid from or into a living body can be improved while minimizing invasion into the living body.

EXAMPLES

Basic Configuration

As an example of the present invention, a pump for ejecting an exudate from the middle ear was constructed with a thin pipe to be contacted with the eardrum, a screw, and a DC motor (manufactured by Mabuchi Motor Co., Ltd.: FA130RA) for rotating the screw.

A rotor to be rotated inside the thin pipe was produced by twisting up two ϕ0.08 mm polyurethane-coated steel wires coated with an ultraviolet curable resin (manufactured by Maruto: Acryl One #1320) and irradiating the twisted wires with ultraviolet rays to bond them together.

Figure 10:
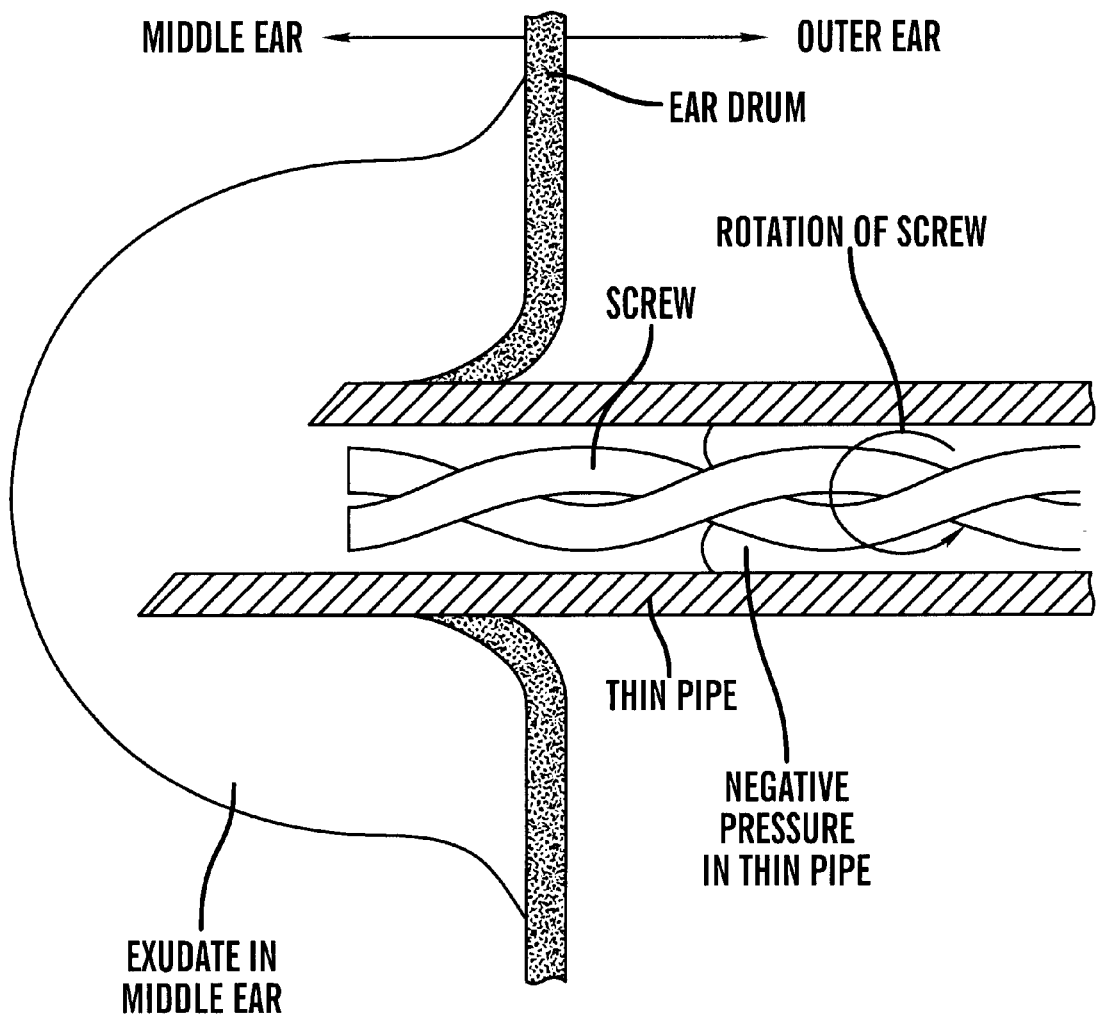
FIG. 10 is a block diagram illustrating suction of an exudate from the middle ear with the screw pump according to the present invention used in the Example.

A method for operating the present pump is shown in FIG. 10. An injection needle was used as the thin pipe and inserted into the eardrum, and a tip of the thin pipe was pushed into the middle ear. Then, a vacuum pump was used to apply a negative pressure to the inside of the thin pipe while a screw mounted to a left tip of a screw mounting section in the thin pipe was rotated in the same direction as the screw twisting direction.

Ejection of Middle Ear Exudate

The pump was used to eject an exudate obtained from the middle ear and installed on a Petri dish. The thin pipe used was a 26G injection needle having an outer diameter ϕ0.45 mm and an inner diameter ϕ0.3 mm (manufactured by Terumo Corporation). When the screw was rotated at 24,000 rpm while applying a negative pressure of −50 cmHg to the inside of the thin pipe, the middle ear exudate, which could not be ejected with a conventional sucking tool of inner diameter ϕ0.7 mm or less, could be ejected in an amount of 80 mm$^3$ in 168 sec. The amount of exudate ejected per unit time was 0.476 mm$^3$/sec.

Ejection of Viscometer Calibration Standard Liquid

A viscometer calibration standard liquid (manufactured by Nihon Grease) in a silicon tube of inner diameter ϕ1 mm was ejected in order to examine the relationships between the viscosity of the liquid and the liquid ejection speed, between the screw rotation speed and the liquid ejection speed, and between the negative pressure in the thin pipe and the ejection speed.

Figure 11:
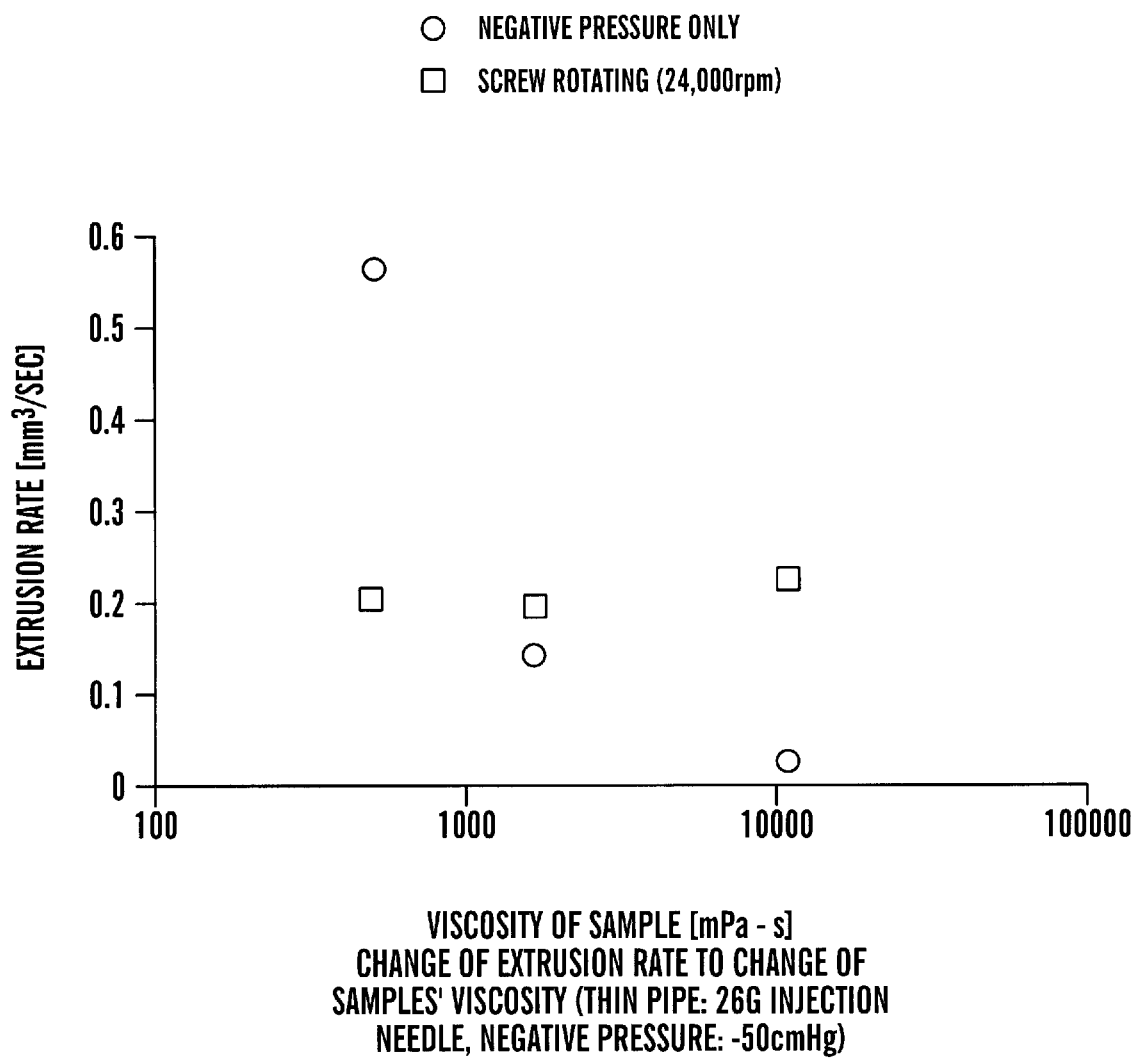
FIG. 11 compares a conventional suction pipe with a screw pump according to the present invention in terms of the ejection capability, using a viscometer calibration standard liquid.

FIG. 11 shows ejection speeds achieved when the liquid had a viscosity of 435.6 mPa·s, 1,767 mPa·s, or 12,270 mPa·s. ○ indicates ejection speeds obtained when the inside of the pipe was subjected to a negative pressure to eject the liquid using only suction, and □ indicates ejection speeds obtained when the inside of the pipe was subjected to a negative pressure while the screw was rotated at 24,000 rpm. The thin pipe was a 26G injection needle, and a negative pressure of −50 cmHg was applied.

When the liquid was ejected using only suction (○), the ejection speed decreased with an increase in viscosity. When, however, the screw was rotated (□), the ejection speed remained at an almost constant value of 0.2 mm$^3$/sec irrespective of the viscosity.

Relationship between Rotation Speed and Ejection Speed

Figure 12:
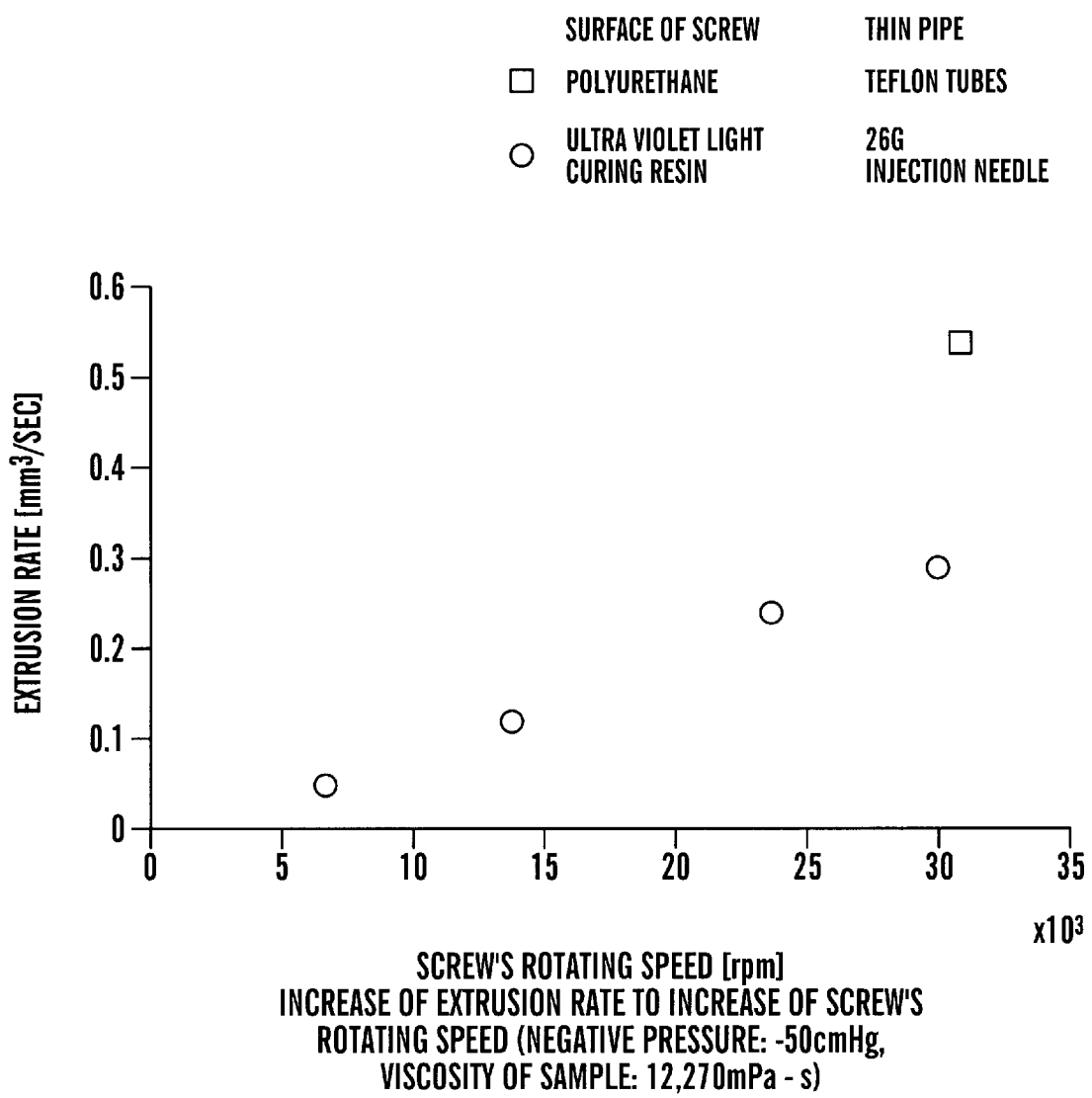
FIG. 12 presents the relationship between the rotation and ejection speeds of the rotator of the screw pump according to the present invention used in the Example.

FIG. 12 shows the relationship between the rotation speed of twisted filaments and the ejection speed. The liquid used was a viscometer calibration standard liquid having a viscosity of 12,270 mPa·s at 20° C. ndicates ejection speeds when a 26G injection needle was used as the thin pipe. □ indicates ejection speeds achieved when a Teflon tube was used as the thin pipe to reduce the friction between the liquid and the inner wall of the thin pipe and twisted filaments with their surface coated with polyurethane were also used to diminish the friction between the liquid and the surface of the screw. When a 26G injection needle was used as the thin pipe (○), the amount of liquid ejected per unit time was 0.28 mm$^3$/sec at a rotation speed of 30,000 rpm, and the ejection amount increased in proportion to the screw rotation speed. In addition, the ejection efficiency was 2.48% when the 100% ejection amount was assumed to be the cross section of the thin pipe minus the cross section of the screw multiplied by the screw pitch and rotation speed.

Relationship between Surface Friction and Teflon Tube and Polyurethane

When a Teflon tube was used as the thin pipe and twisted filaments with their surface coated with polyurethane were used as the screw (□), the ejection amount per unit time was 0.523 mm$^3$/sec at a rotation speed of 30,000 rpm, which is 1.9 times as large as a value obtained by a tool using a 26G injection needle as the thin pipe and having a screw with its surface coated with an ultraviolet curable resin.

Relationship between Negative Pressure and Ejection Speed

Figure 13:
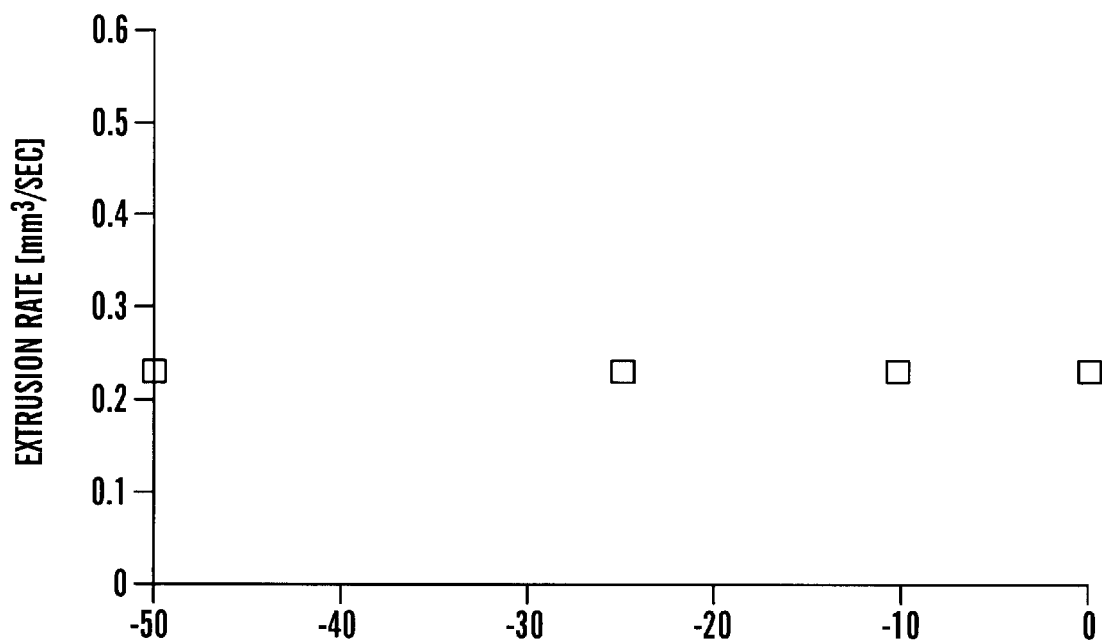
FIG. 13 presents the relationship between the negative pressure in the screw pump and the ejection speed thereof according to the present invention used in the Example.

FIG. 13 shows variations in ejection amount observed when the negative pressure exerted inside the thin pipe was varied. The liquid used was a viscometer calibration standard liquid having a viscosity of 12,270 mPa·s at 20° C., and the twisted filaments rotation speed was set at 24,000 rpm. The negative pressure was set at −50, −25, −10, or 0 cmHg for each measurement, but no significant difference was observed in ejection speed.

The results of these experiments indicated that the present pump can eject liquids of viscosity of 500 to 12,000 mPa·s at almost the same ejection speed.

In addition, the ejection speed of the present pump does not depend on the negative pressure of the inside of the thin pipe but heavily on the rotation speed of the twisted filaments, the frictions between the liquid and the thin pipe, and frictions between the liquid and the screw.

Screw Angle

Figure 14:
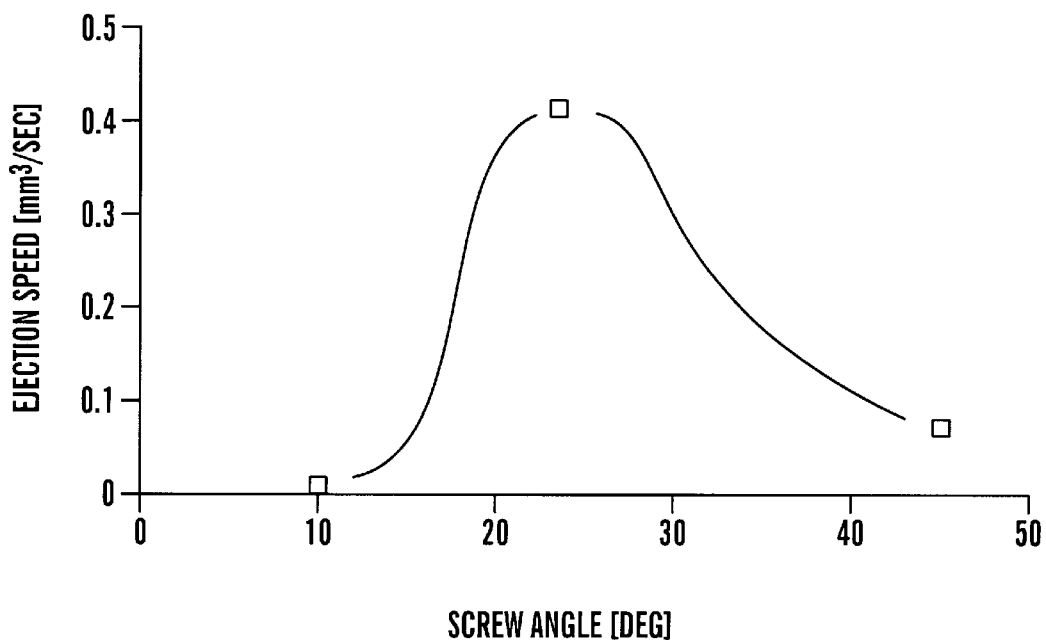
FIG. 14 presents the relationship between the screw angle and ejection speed of the rotator of the screw pump according to the present invention used in the Example.

FIG. 14 shows the relationship between the angle of the screw of the rotor and the ejection speed. This figure indicates that the ejection speed is particularly high at a screw angle between about 15 and 35°.

Figure 15:
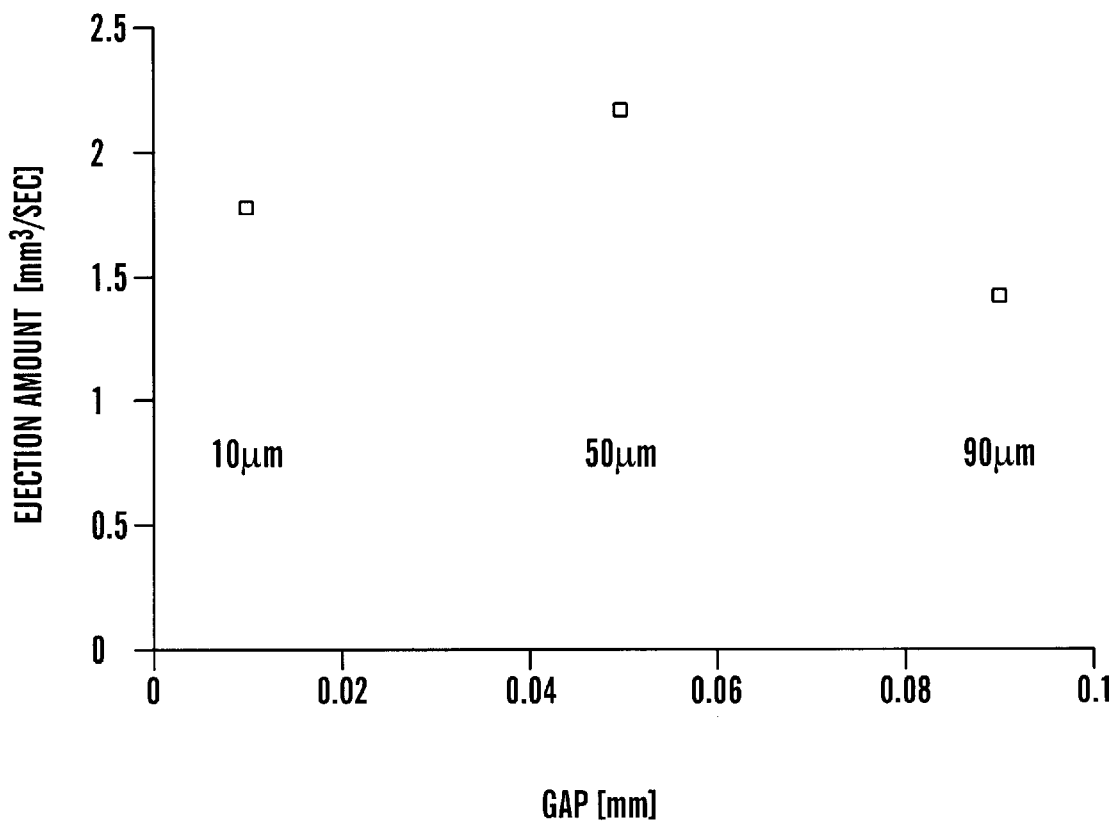
FIG. 15 presents the relationship between the amount of liquid ejected and the size of the gap between the outer periphery of the rotator and the inner wall of the pipe in the screw pump according to the present invention used in the Example.

Relationship between Ejection Amount and Gap between Rotator Outer Periphery and Pipe Inner Wall FIG. 15 shows the relationship between the ejection amount and the gap between the outer periphery of the rotor and the inner wall of the pipe. This figure indicates that the amount of liquid ejected is not significantly affected even if the gap between the rotator outer periphery and the pipe inner wall is set to be larger than the thickness of a liquid layer flowing through the pipe.

These results indicate that the gap in the pipe can be arbitrarily set to facilitate assembly of the screw pump of a very small diameter.

Effects

In order to eject a viscous exudate from the middle ear while minimizing invasion into the eardrum, a micropump was designed and experimentally produced which applies a negative pressure to the inside of a thin pipe while rotating a screw therein. This pump was used to apply a negative pressure of −50 cmHg to the inside of a thin pipe that was a 26G injection needle of outer diameter φ0.45 mm and inner diameter φ0.3 mm while rotating a screw in the thin pipe at 24,000 rpm. Then, the middle ear exudate, which could not be ejected with a tool of inner diameter φ0.7 mm or less which was only capable of suction, could be ejected at an ejection speed of 0.476 mm$^3$/sec.

What is claimed is:

1. A needle-shaped precision screw pump of a very small diameter for injecting or ejecting a liquid into or from a biological tissue comprising a cylindrical thin needle and a rotor housed in said needle for rotation along an axial direction thereof, said rotor comprising a plurality of filaments twisted together.

2. A precision screw pump in an instrument for injecting or ejecting a liquid into or from a biological tissue, comprising a cylindrical thin needle having an introduction port at one end and a discharge port at the other end, a cylinder connected to one end of the needle and having a larger diameter than the needle, a rotor housed in said needle for rotation along an axial direction thereof, and a driver housed in said cylinder and connected to one end of said rotor for rotating the rotor, wherein said rotor comprises a plurality of filaments twisted together and is rotated in synchronism with the rotation of said driver to transfer a liquid through said thin needle from said introduction port to said discharge port.

3. The precision screw pump according to claim 2 wherein said cylindrical needle comprises a smooth-surface substance having a predetermined strength.

4. The precision screw pump according to claim 2 wherein the filaments constituting said rotor are covered with the smooth-surface substance.

5. The precision screw pump claim 2 wherein said rotor has a screw angle set between 15 and 35° relative to a rotational center axis.

6. The precision screw pump according to claim 2, wherein said cylindrical needle has a small diameter in proportion to a diameter of the rotor.

7. The precision screw pump according to claim 6, wherein said cylindrical needle has an inner diameter of 0.03 mm.

8. The precision screw pump according to claim 2, wherein each of said plurality of filaments is a steel wire.

9. A rotor for a screw pump comprising a plurality of filaments twisted together wherein said filaments are coated with an adhesive and said rotor has a screw angle set between about 15° and 35° relative to a rotational center axis of said rotor.

10. A method for producing a screw pump rotor including a plurality of adhesive-coated filaments, the method comprising:

providing a plurality of filaments;

coating an adhesive on the plurality of filaments;

twisting the plurality of filaments together; and curing the adhesive to form the screw pump rotor.

11. The method according to claim 10, wherein the adhesive is a photocurable resin.

12. A biological liquid injection and ejection instrument comprising a micro screw pump comprising a thin cylindrical hollow needle and a rotor housed in said needle for rotation along an axial direction thereof, said rotor comprising a plurality of filaments twisted together.

13. A biological liquid injection and ejection instrument comprising a micro screw pump comprising a thin cylindrical hollow needle and a rotor housed in said needle for rotation along an axial direction thereof, said hollow needle having a small diameter in proportion to a diameter of said rotor.

14. A needle-shaped precision screw pump of a very small diameter for injecting or ejecting a liquid into or from a biological tissue comprising a cylindrical thin needle and a rotor housed in said needle for rotation along an axial direction thereof, said cylindrical thin needle having a small diameter in proportion to a diameter of the rotor.

15. A precision screw pump in an instrument for injecting or ejecting a liquid into or from a biological tissue, comprising:

a cylindrical thin needle having an introduction port at one end and a discharge port at the other end;

a cylinder connected to one end of the needle and having a larger diameter than said needle;

a rotor housed in said needle for rotation along an axial direction thereof; and a driver housed in said cylinder and connected to one end of said rotor;

wherein said cylindrical thin needle has a small diameter in proportion to a diameter of said rotor and said rotor is rotated in synchronism with the rotation of said driver to transfer a liquid through said needle from said introduction port to said discharge port.

16. The precision screw pump according to claim 15, wherein said rotor comprises a plurality of filaments twisted together.

17. The precision screw pump according to claim 16, wherein the plurality of filaments constituting said rotor are covered with the smooth-surface substance.

18. The precision screw pump according to claim 16, wherein said rotor has a screw angle set between 15° and 35° relative to a rotational center axis.

19. The precision screw pump according to claim 16, wherein each of the plurality of filaments is a steel wire.

20. The precision screw pump according to claim 15, wherein said needle has an inner diameter of 0.03 mm.

21. The precision screw pump according to claim 15, wherein said needle comprises a smooth-surface substance having a predetermined strength.

* * * * *